United States Patent [19]

Lee

[11] Patent Number: 4,781,190
[45] Date of Patent: Nov. 1, 1988

[54] METHOD OF ARTHROSCOPIC REPAIR OF A LIMB JOINT

[76] Inventor: Wilson K. C. Lee, 14 Thornber Street, Unley Park 5061 South Australia, Australia

[21] Appl. No.: 850,702

[22] Filed: Apr. 11, 1986

[30] Foreign Application Priority Data

Jun. 18, 1985 [AU] Australia .............................. PH1081

[51] Int. Cl.⁴ ....................... A61B 17/04; A61B 17/06
[52] U.S. Cl. ................................. 128/334 R; 128/339; 128/335
[58] Field of Search ................... 128/339, 334 R, 340, 128/335

[56] References Cited

U.S. PATENT DOCUMENTS

| | | | |
|---|---|---|---|
| 2,516,710 | 7/1950 | Mascolo | 128/339 |
| 2,833,284 | 5/1958 | Springer | 128/340 |
| 4,512,346 | 4/1985 | Lemole | 128/335 |
| 4,597,390 | 7/1986 | Mulhollan et al. | 128/340 |
| 4,602,635 | 7/1986 | Mulhollan et al. | 128/334 R |

FOREIGN PATENT DOCUMENTS 867420 1/1953 Fed. Rep. of Germany .

OTHER PUBLICATIONS

"Suture of New and Old Peripheral Meniscus Tears" by Per Hamberg, M.D. et al., Linkoping, Sweden, J. of Bone and Joint Surg., vol. 65A, p. 193, (1983).
"Arthroscopic Meniscal Repair" by Clancy and Graf, M.D.
"Meniscal Repair" by Barber & Stone, J. of Bone and Joint Surg., vol. 67B, p. 39, (1985).
"The Acufex Big Bend Stitcher—Position is Everything"; L. Crane.
"A Technique of Arthroscopic Meniscal Repair", Lawrence Crane, M.D.

Primary Examiner—Richard C. Pinkham
Assistant Examiner—Gary Jackson
Attorney, Agent, or Firm—Cushman, Darby & Cushman

[57] ABSTRACT

A method of surgical repair using a needle having two sharpened ends, under arthroscopic control by passing a needle into the joint until the eye of the needle just emerges from the skin on the distal side of the joint, then pulling the suture through the joint to the outside while the needle remains partially within the joint capsule and passing the needle back to the opposite side of the joint so as to reverse the maneuver, so that the needle remains partially within the joint capsule.

13 Claims, 6 Drawing Sheets

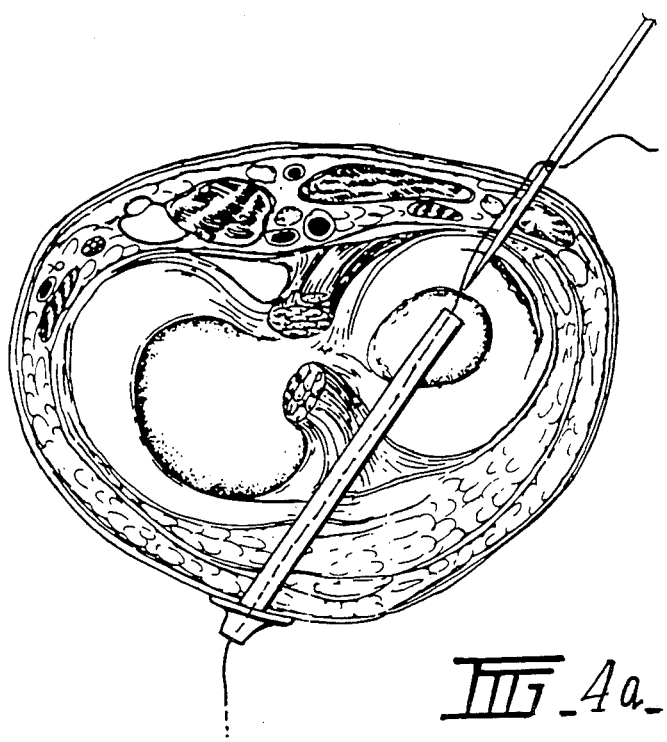
FIG_4a_
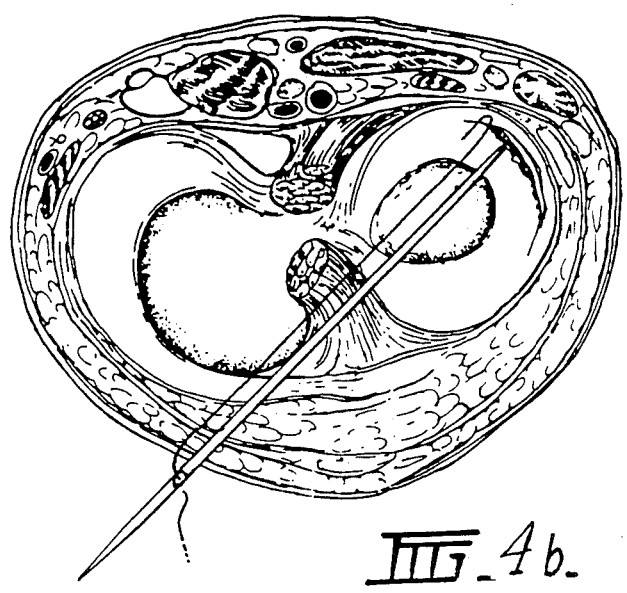
FIG_4b_

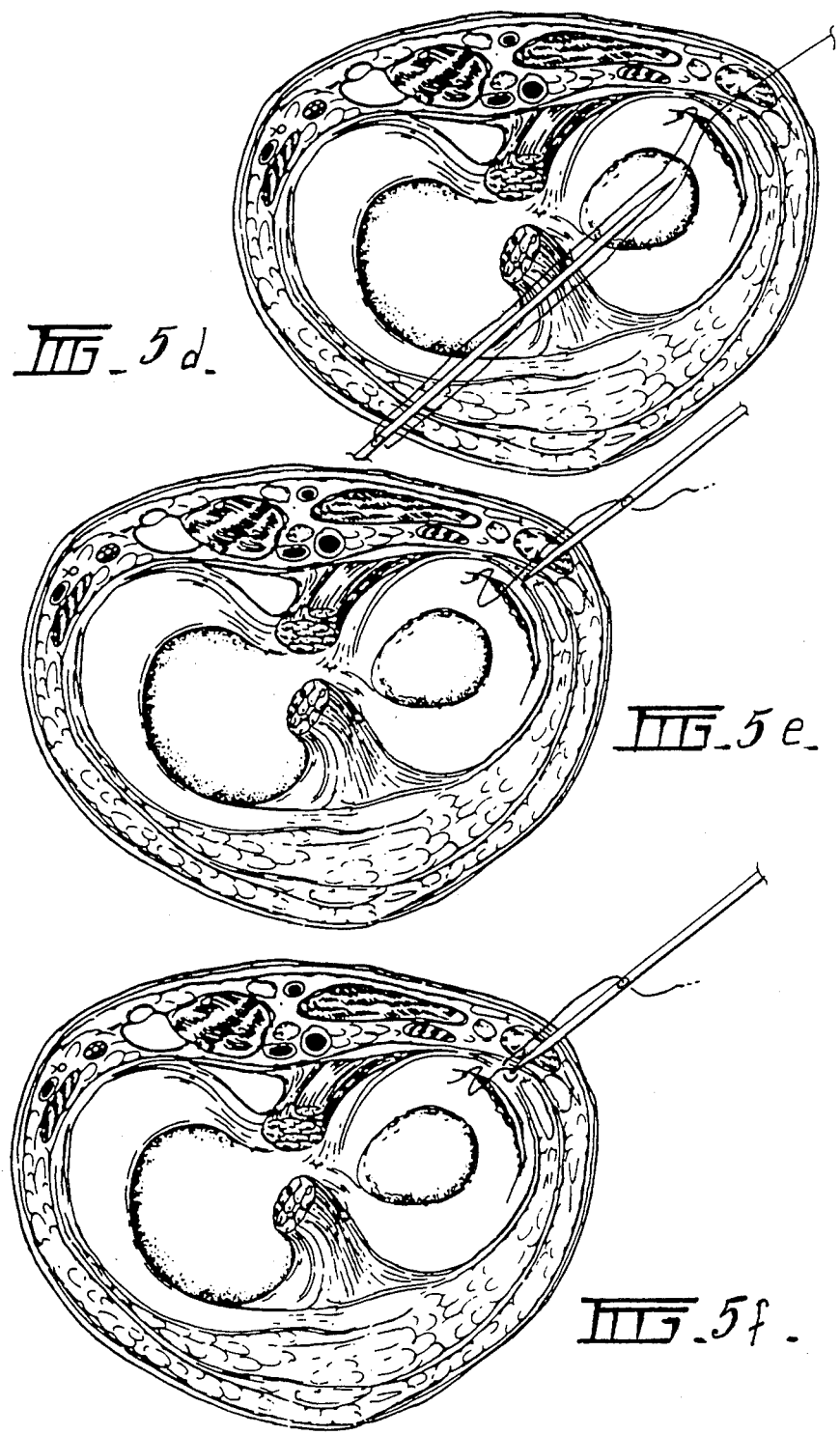
FIG_5d.
FIG_5e.
FIG_5f.

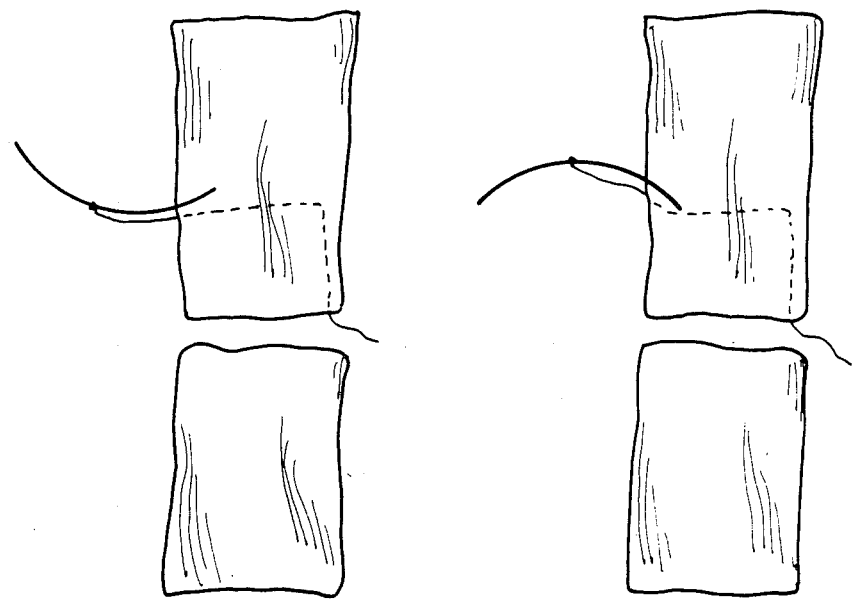
FIG._6e_  FIG._6f_
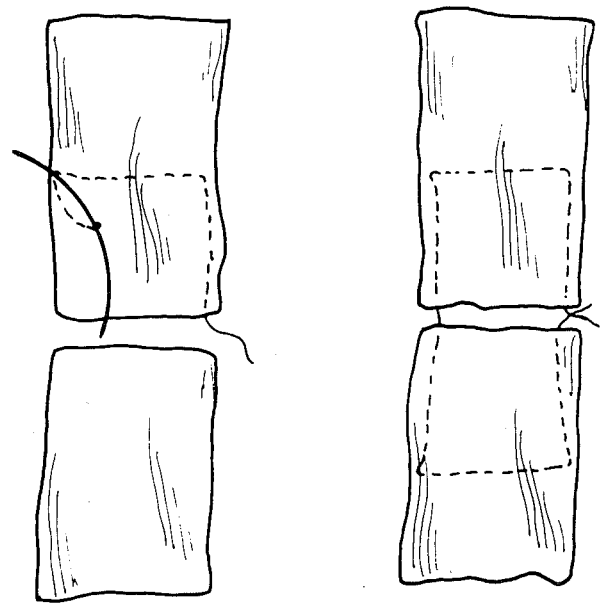
FIG._6g_  FIG._6h_

METHOD OF ARTHROSCOPIC REPAIR OF A LIMB JOINT

This invention relates to improvements in or relating to surgical needles.

Advances in surgery depend in part on the availability to surgeons of instruments suitable for use in confined spaces.

It is an object of the present invention to provide a method and use of a needle for suturing which enables surgical sutures to be inserted in a structure within a confined anatomical site, without the necessity for knotting the sutures externally to that site.

The present invention is particularly useful in the repair of lesions of the meniscus of the knee joint, and will accordingly be described in more detail in relation to that field of use. However, its usefulness in other fields will be apparent and it will be understood that the invention is not limited to use only in this context. For example, applications in the fields of urology and laparoscopic abdominal surgery are contemplated.

Preferred embodiments of the invention will be further illustrated by the following non-limiting examples, with reference to the accompanying figures, in which:

FIGS. 4a and 4b represents diagrammatically the principle of operation of the needle of the invention;

FIGS. 5a, 5b, 5c, 5d, 5e and 5f represent diagrammatically the use of the straight needle of the invention for repair of a meniscal tear; and FIGS. 6a, 6b, 6c, 6d, 6e, 6f, 6g and 6h represent diagrammatically the use of the curved needle of the invention for repair of a tendon.

Figure 1:
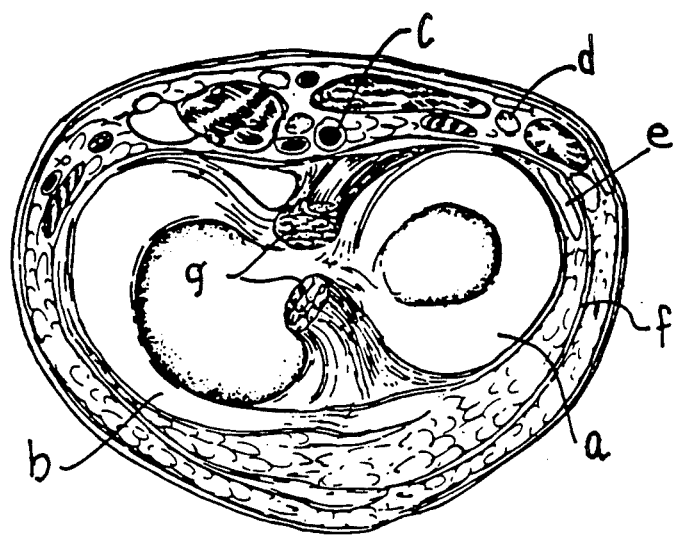
FIG. 1 represents a diagrammatic view of a transverse section through the human knee joint as seen from above.

Tears in the meniscal cartilage of the knee joint are among the most common injuries presenting to orthopaedic surgeons. They are particularly common among sportsmen and women, especially footballers. As shown in FIG. 1, in each knee there are two meniscal cartilages, the lateral meniscus (a) and the medial meniscus (b). Both of these menisci are vulnerable to tearing or rupture caused by torsional stress. Such meniscal lesions are frequently associated with injuries to the cruciate ligaments (FIG. 1g).

Although at one time total or partial meniscectomy was the only available treatment for injuries of this type, it has become recognized that removal of the meniscus leads in many cases to subsequent degenerative arthritis of the knee joint (Jackson, J. P.: Brit. Med. J. (1968) 2 525-527). Although initial attempts at surgical conservation of the meniscus necessitated open surgery of the knee joint (Hamberg, P. J. Gillquist, and J. Lysholm: J. Bone and Joint Surgery (1983) 65A, 193-197), with consequent risk of infection and prolonged recovery time, more recently it has been shown that it is possible to perform the repair using an arthroscopic technique (Barber, F. A. and R. G. Stone J. Bone and Joint Surgery (1985) 67B 39-41), employing two needles carrying a single suture thread.

Such operations are now commonly performed. Special needle holders are used (Barber and Stone, op. cit) or alternatively specially designed single or double channeled cannulas (Crane, L.: Clancy, W. G. J. and B. K. Graf: technical papers supplied with products) may be used. "Meniscal Stitcher" instruments are commercially available, for example the Acufex "Big Bend" stitcher and meniscal stitcher based on the second and third references cited in this paragraph ("Acufex" is a trade mark of Acufex Microsurgical, Inc., Massachusetts, U.S.A.).

All of the above described techniques present two major disadvantages. Firstly, it is not possible to knot the sutures within the joint space, and so the knots must be placed either externally to the joint capsule, (FIG. 1f) necessitating a skin incision and dissection down to the capsule, or outside the skin over a sponge and button. The latter may result in chafing and maceration of the skin.

Secondly, the sites of egress of the needle from the joint are limited by the necessity to avoid damage to structures such as the popliteal artery (FIG. 1c) and the common peroneal nerve (FIG. 1d).

I have now developed a surgical needle which overcomes the limitations presented by those heretofore known.

Figure 2:
FIG. 2 represents a perspective view of the preferred embodiment of the invention.

According to one preferred embodiment of the present invention there is provided a surgical needle having two sharpened ends together with a centrally or eccentrically placed eye aperture. This is illustrated in FIG. 2.

According to a second preferred embodiment, there is provided an atraumatic needle having two sharpened ends, in which the suture material is attached to the needle at a centrally or eccentrically placed site.

The material of the needle may be substantially rigid. Alternatively it may be partially flexible, so as to allow the needle to be used optionally in conjunction with a slightly curved cannula.

The ends of the needle may be of trocar type, or have a cutting edge.

Preferably the needle is made of surgical grade stainless steel.

A large range of sizes of needle may be used, depending upon the particular site of surgery, ranging from approximately 0.5 cm for microsurgical applications to 20-15 cm for orthopaedic surgery.

According to one particularly preferred embodiment, the needle is straight and has length in the range 15-25 cm, with the eye of the needle at approximately ⅔ to 5/7 of the length from one end. Preferably the length is 18 cm.

Figure 3:
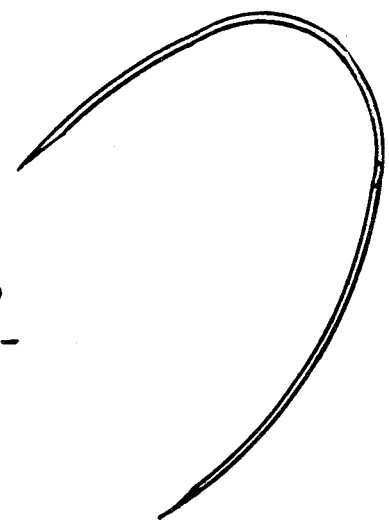
FIG. 3 represents a perspective view of another preferred embodiment of the invention.

According to a second particularly preferred embodiment, the needle is curved, having two sharpened ends and the eye aperture placed midway along the length of the needle. This is illustrated in FIG. 3. A wide range of radii of curvature may be used from approximately 0.25 cm to infinity. The ends of the needle may be of trocar type or have a cutting edge.

The needle is suitable for use with any known type of suture material.

The present invention supplies a long-felt want with its capacity, simplicity and reliability, and it constitutes a significant advance in the procedures of tissue repair in a confined space.

FIG. 3 shows the advantage of the eccentrically placed eye aperture of one preferred embodiment of the invention. If the needle is passed into the knee joint through a cannula into the anterior medial aspect of the knee until the eye of the needle just leaves the skin on the posterior lateral side of the knee, the suture can be pulled through to the outside. However, the needle itself remains partly within the joint capsule (FIG. 3a). The needle can then be passed back to the anterior medial side of the knee, thus reversing the maneuver, with the needle again remaining partly inside the joint capsule (FIG. 3b).

EXAMPLE 1

Repair of a Peripheral Tear in the Lateral Meniscus

The straight needle, carrying a suture previously knotted at one end, is inserted via the end distal from the eye into the knee joint at the anterior medial aspect of the joint. Entry may be either directly through the skin, or more conveniently may be via the arthroscopic entry portal. Optionally a cannula may be used for greater accuracy in directing the needle. Under arthroscopic control using either direct vision or television monitor control, the tip of the needle is advanced until it reaches the medial side of the tear (FIG. 4a).

The needle is then pushed through the meniscus and advanced so that the trailing tip of the needle remains inside the joint capsule, and the eye of the needle is just outside the skin of the knee on the lateral side, as shown in FIG. 4b. The free end of the suture is pulled through to the exterior of the knee, as shown in FIG. 4c. The needle is then pushed back through the meniscus in the reverse direction until the eye of the needle is just outside the skin and the tip of the longer arm of the needle is just adjacent to the meniscus, as shown in FIG. 4d. Optionally the tip of the needle may remain within the meniscal tissue. The suture is pulled through to the exterior of the knee as before. The procedure is repeated as many times as required to repair the tear, as shown in FIG. 4e.

Knots may be tied in the suture at intervals, either by passing the needle through a loop in the suture (FIG. 4f), or, if the suture is not a monofilament material, by passing the needle through the suture material itself. Other methods of forming knots in the suture may also be used. The knots thus formed are within the joint itself.

A further advantage of the use of the needle of the present invention for such procedures is that if a structure such as a nerve, tendon or blood vessel is traversed by the needle, the suture may be pulled through without further damage to that structure.

EXAMPLE 2

Repair of Ligaments or Tendons

Ligaments or tendons may be repaired by similar procedures to those described in Example 1, using either straight or curved needles according to the present invention. In the case of tendons in the hand, repair may be effected using the needle of the present invention without opening or suturing the tendon sheath.

Although the preferred embodiments of the invention have been described in detail it will be understood that many variations in the specific details thereof will be obvious to persons skilled in the art and the invention in its broader aspects contemplates all such variations falling within the more general disclosure hereinabove.

EXAMPLE 3

Repair of Rotator Cuff Ligament in the Shoulder

The needle (either straight or curved) is passed through the skin either directly or via a cannula into the subacromial space. Using either direct vision or orthoscopic control, the needle is directed at the rotator cuff ligament from one side of the tear to the other. The tear is stitched as described for meniscus in Example 1. Interrupted sutures may be used.

EXAMPLE 4

Repair of Tendons

Tendons may be sutured preferably using the curved needle according to the invention, either in an open procedure or under arthroscopic control.

Figures 5A, 5B, 5C:
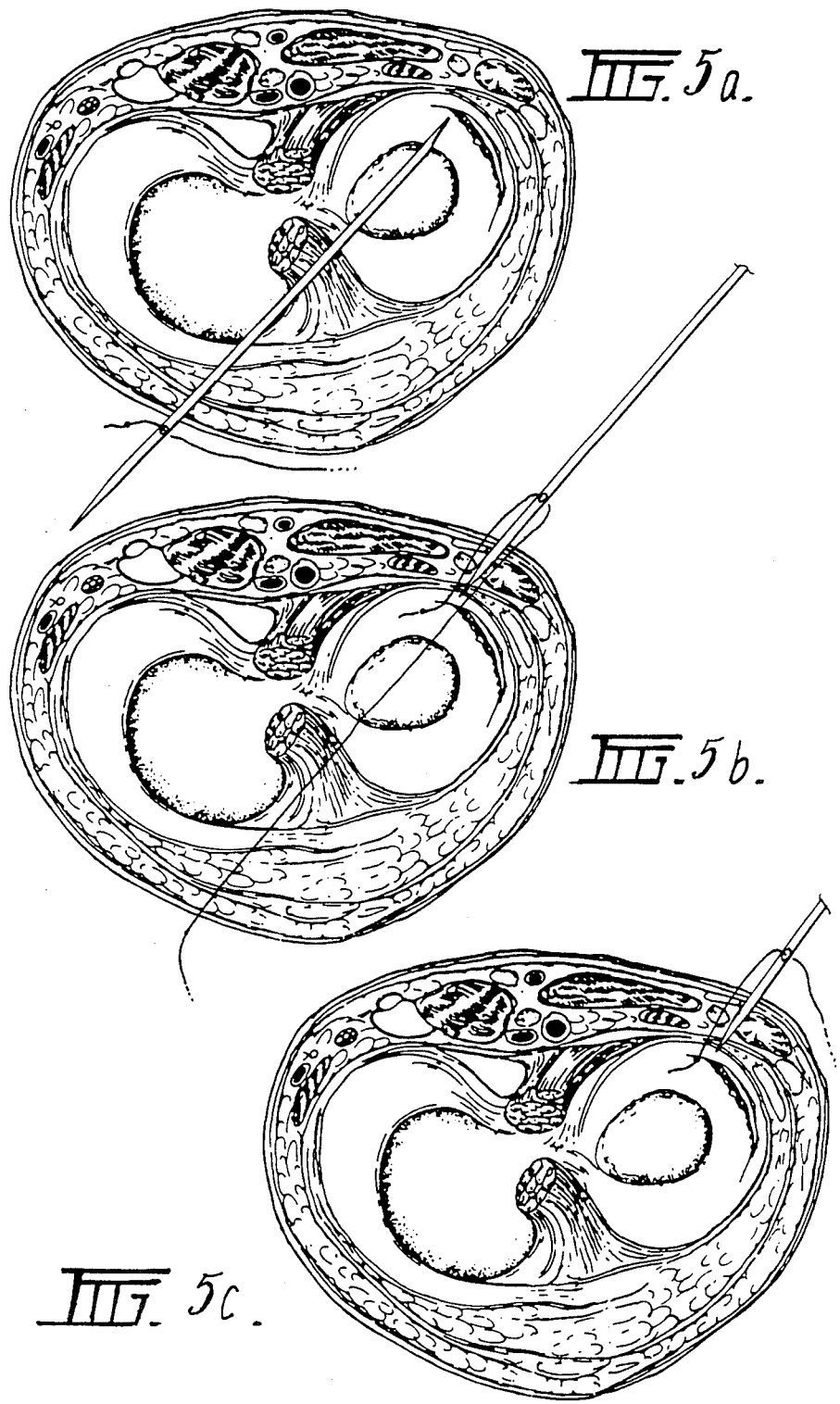
Figure 6A:
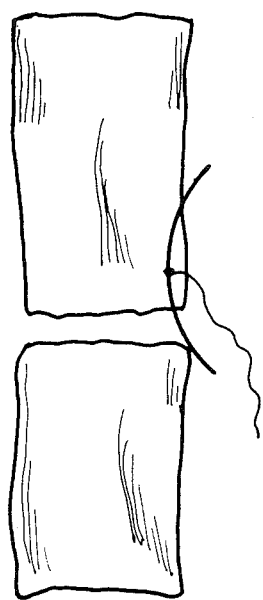
Figure 6B:
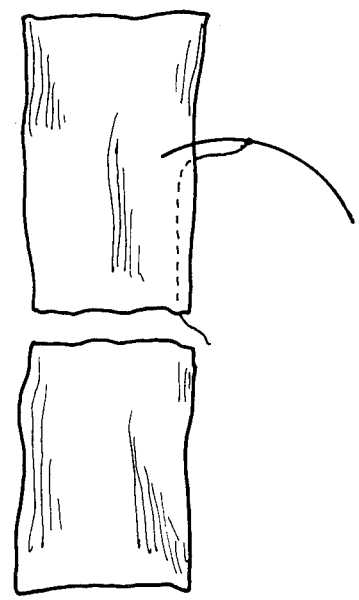
Figure 6C:
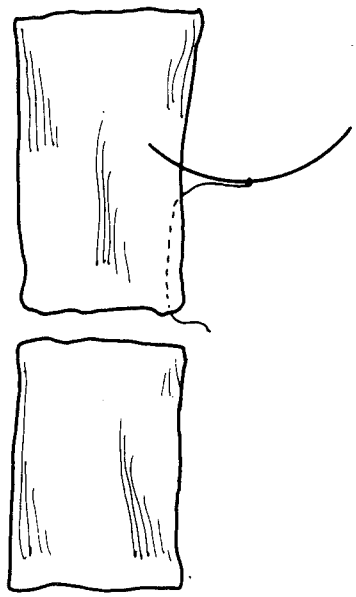
Figure 6D:
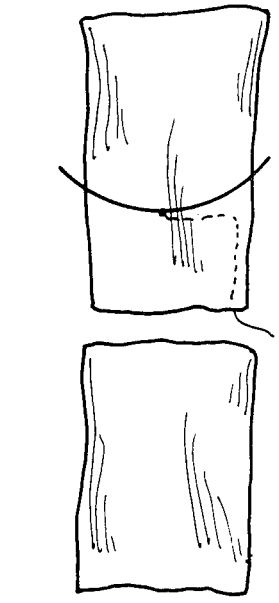

The needle is first passed through one cut end of the tendon, exiting from the side of the tendon (FIG. 5a). With the trailing tip of the needle still inside the tendon, the direction of the needle is changed as shown in FIG. 5c and d. The dotted line represents the path of the suture. The needle is then passed through the tendon to the other side as shown in FIG. 5d and e, so that the trailing tip of the needle again remains within the tendon. The direction of the needle is changed again so that the leading tip is directed at the cut end of the tendon (FIG. 5f and g). The same procedure is repeated for the other cut end of the tendon. By this procedure the suture material is entirely retained within the tendon tissue, and is invisible. The final knot may be tied between the cut ends so that the knot is also hidden (FIG. 5h).

I claim:

1. A method for surgical repair, under arthroscopic control, of a lesion in a tissue of a limb joint of a mammal comprising the steps of:
    (a) inserting a straight needle, carrying a suture previously knotted at one end, via the end distal from an eccentrically placed eye aperture into the joint at the anterior medial aspect of the joint,
    which needle has two tapered, sharpened ends and is 0.5 to 30 cm long;
    (b) advancing the tip of the needle under arthroscopic control using either direct vision or television monitor control, until it reaches the medial side of the tear;
    (c) pushing the needle through the tissue and advancing it so that the trailing tip of the needle remains inside the joint capsule and the eye aperture of the needle is just outside the skin of the joint on the lateral side;
    (d) pulling the free end of the suture through to the exterior of the joint;
    (e) pushing the needle back through the tissue in the reverse direction until the eye aperture of the needle is just outside the skin and the tip of the longer arm of the needle is just adjacent to the tissue;
    (f) pulling the suture through to the exterior of the joint as in step (d); and
    (g) repeating the procedure as many times as required to repair the lesion.

2. A method according to claim 1 wherein the lesion is in a ligament.

3. A method according to claim 1 wherein the lesion is in a rotator cuff of a shoulder.

4. A method according to claim 1 wherein the lesion is in a tendon.

5. A method according to claim 4 wherein the tendon is a flexor tendon.

6. A method according to claim 4 wherein the tendon is an Achilles tendon.

7. A method for repair of a peripheral tear in the lateral meniscus of the tibiofemoral joint of a mammal; comprising the steps of:

(a) inserting a straight needle, carrying a suture previously knotted at one end, via the end distal from an eccentrically placed eye aperture into the knee joint at the anterior medial aspect of the joint, which needle has two tapered, sharpened ends and is 0.5 to 30 cm long;

(b) advancing the tip of the needle under arthroscopic control using either direct vision or television monitor control, until it reaches the medial side of the tear;

(c) pushing the needle through the meniscus and advancing it so that the trailing tip of the needle remains inside the joint capsule and the eye aperture of the needle is just outside the skin of the knee on the lateral side;

(d) pulling the free end of the suture through to the exterior of the knee;

(e) pushing the needle bach through the meniscus in the reverse direction until the eye aperture of the needle is just outside the skin and the tip of the longer arm of the needle is just adjacent to the meniscus;

(f) pulling the suture through to the exterior of the knee as in step d; and (g) repeating the procedure as many times as required to repair the tear.

8. A method for repair according to claim 7 wherein said needle consists essentially of surgical grade stainless steel.

9. A method according to claim 2 wherein the needle is passed into the joint directly through the skin.

10. A method according to claim 7 wherein the needle is passed into the joint through a cannula.

11. A method according to claim 7 wherein the needle is passed into the joint via an arthroscopic entry portal and in which a cannula is optionally used.

12. A method according to claim 7 wherein the end of the needle remains within the meniscal tissue.

13. A method according to claim 7 wherein the suture is knotted at intervals, so that knots are within the joint cavity.

* * * * *